(12) United States Patent
Karlinsey (10) Patent No.: US 8,556,553 B2
(45) Date of Patent: Oct. 15, 2013

(54) HYBRID ORGANIC/INORGANIC CHEMICAL HYBRID SYSTEMS, INCLUDING FUNCTIONALIZED CALCIUM PHOSPHATE HYBRID SYSTEMS, AND A SOLID-STATE METHOD FOR PRODUCING THE SAME

(75) Inventor: Robert L. Karlinsey, Indianapolis, IN (US)

(73) Assignee: Indiana Nanotech LLC, Indianapolis, IN (US)

( * ) Notice: Subject to any disclaimer, the term of this patent is extended or adjusted under 35 U.S.C. 154(b) by 953 days.

(21) Appl. No.: 12/018,627

(22) Filed: Jan. 23, 2008

(65) Prior Publication Data

US 2008/0187500 A1    Aug. 7, 2008

Related U.S. Application Data

(60) Provisional application No. 60/888,354, filed on Feb. 6, 2007, provisional application No. 60/891,849, filed on Feb. 27, 2007, provisional application No. 60/941,095, filed on May 31, 2007.

(51) Int. Cl.
| | |
|---|---|
| *A61K 9/50* | (2006.01) |
| *B23C 1/00* | (2006.01) |
| *A61K 9/16* | (2006.01) |
| *A61K 6/00* | (2006.01) |
| *C01F 11/00* | (2006.01) |
| *C08K 3/32* | (2006.01) |

(52) U.S. Cl.
CPC .............. *A61K 9/16* (2013.01); *A61K 9/1611* (2013.01); *A61K 9/1617* (2013.01); *A61K 6/0082* (2013.01); *C01F 11/00* (2013.01); *C08K 2003/325* (2013.01); *B23C 2220/00* (2013.01)
USPC ................ 409/64; 424/57; 424/489; 424/52

(58) Field of Classification Search
USPC ....................................... 623/23.36
See application file for complete search history.

(56) References Cited

U.S. PATENT DOCUMENTS

| | | | |
|---|---|---|---|
| 3,190,568 A | 6/1965 | Freedman et al. | |
| 3,876,160 A | 4/1975 | Bloch | |
| 4,018,619 A | 4/1977 | Webster et al. | |
| 4,677,140 A | 6/1987 | Shioitsu | |
| 5,342,441 A * | 8/1994 | Mandai et al. | 106/35 |
| 5,833,954 A | 11/1998 | Chow et al. | |
| 6,053,970 A | 4/2000 | Ison et al. | |
| 6,126,097 A * | 10/2000 | Chen et al. | 241/27 |
| 6,334,583 B1 * | 1/2002 | Li | 241/175 |
| 6,840,961 B2 | 1/2005 | Tofighi et al. | |
| 2002/0037258 A1 * | 3/2002 | Dodd et al. | 424/49 |
| 2003/0069638 A1 | 4/2003 | Barlow et al. | |
| 2003/0120351 A1 * | 6/2003 | Tofighi et al. | 623/23.62 |
| 2004/0101494 A1 | 5/2004 | Scott et al. | |
| 2005/0025721 A1 | 2/2005 | Holme et al. | |
| 2005/0241535 A1 * | 11/2005 | Bohner | 106/690 |
| 2006/0175443 A1 * | 8/2006 | Bysouth | 241/30 |
| 2006/0270752 A1 | 11/2006 | Xu et al. | |
| 2007/0059379 A1 | 3/2007 | Gerber | |
| 2007/0149650 A1 | 6/2007 | Masuda | |
| 2007/0178220 A1 | 8/2007 | Karlinsey | |
| 2007/0183984 A1 | 8/2007 | Haas et al. | |
| 2008/0187500 A1 | 8/2008 | Karlinsey | |

OTHER PUBLICATIONS

Minari et al., The Effect on the fatigue strength of bone cement of adding Sodium Fluoride, 2001, Proc. Instn. Mech. Engrs., vol. 215, Part H, pp. 251-253.*

* cited by examiner

*Primary Examiner* — Frederick Krass
*Assistant Examiner* — Isaac Shomer
(74) *Attorney, Agent, or Firm* — Brannon Sowers & Cracraft PC (57) ABSTRACT

A solid-state method of producing functionalized moieties, including placing predetermined amounts of inorganic and inorganic materials and milling media into a vessel rotatably connected to a turntable platform, an amount of an organic material into the vessel, rotating the vessel in a first direction while turning the turntable platform in a second direction counter to the first direction, milling the inorganic and organic materials into smaller respective organic and inorganic particles, and fusing portions of organic particles to inorganic parties to define functionalized moieties. The inorganic material may include calcium phosphates of varying phases, structure, and composition. The organic material may include anionic surfactants, cationic surfactants, neutral surfactants, carboxylic acids, polymers, copolymers, block copolymers, and combinations thereof.

13 Claims, 4 Drawing Sheets

Fig. 4 ns results from remin/demin cycling study including a
HYBRID ORGANIC/INORGANIC CHEMICAL HYBRID SYSTEMS, INCLUDING FUNCTIONALIZED CALCIUM PHOSPHATE HYBRID SYSTEMS, AND A SOLID-STATE METHOD FOR PRODUCING THE SAME

CROSS-REFERENCE TO RELATED APPLICATIONS

This application claims priority to U.S. provisional patent application Ser. No. 60/888,354, filed Feb. 6, 2007; U.S. provisional patent application Ser. No. 60/891,849, filed Feb. 27, 2007; and U.S. provisional patent application Ser. No. 60/941,095, filed May 31, 2007, each of which are incorporated herein in their entirety by reference.

TECHNICAL FIELD

The present novel technology relates generally to the field of chemical synthesis, and more particularly, to a method and system for producing functionalized hybrid moieties without the need for sophisticated chemistries.

BACKGROUND

Preventing caries and cavities and improving the delivery of minerals necessary to healthy teeth and bone, while preserving and/or enhancing cosmetic features, are important goals in oral health care. In this regard the application of calcium and other mineral-containing agents continues to be an effective and widely used treatment for the prevention of cavities and remineralization of teeth and bone. Although effective in most cases, it is not without its drawbacks. Conventional mineral treatments are only marginally effective in providing useful minerals to teeth and enamel, and a large proportion of the so-applied minerals are unabsorbed and passed on into, and ultimately through, the body.

Clearly then, there is a need for mineral delivery compounds that can help prevent cavities and that can also aid in the reconstruction of damaged teeth and bone. There is also a continuing need for materials that exhibit high absorption characteristics. Various embodiments discussed herein address these needs.

With respect to the production of functionalized materials, there are few practical chemical processes that allow for industry-sized scaling. These techniques, as well as other well-known chemistries, include hydrothermal/solvothermal synthesis, micellar templates, and controlled growth in hot volatile solvents. Although these and other chemistries exist for creating functionalized materials, they are generally characterized by one or more of the following drawbacks: 1) wide temperature variations, 2) need for volatile solvents to effectuate dissolution of one or more phases, 3) reduced pressure systems to alleviate oxygen or water contact with reagents, 4) expensive templating molecules or multi-step syntheses, and 5) excessive overhead, including scientific expertise, laboratory space, and equipment.

Thus, there remains a need for a process for more efficiently producing functionalized materials, such as micro-, meso, and nanoscale organic/inorganic hybrid composites, without the use of solvents and on a large, industrial scale. These functionalized materials may compliment new and/or existing dental product formulations (with or without fluoride), such as gels, varnishes, pastes, rinses, adhesives, filling materials and the like, for the repair of weakened dentition. The present novel technology addresses these needs.

SUMMARY

The present novel technology relates generally to the production of functionalized hybrid moieties without the need for sophisticated chemistries, and, more particularly to a solid-state method for producing the same.

One object of the present novel technology is to provide an improved method for producing functionalized hybrid moieties for the purposes of delivering superior performance in oral care product formulations in the absence or presence of fluoride. Further objects, features, and advantages will become apparent from a consideration of the following description and accompanying drawings.

DETAILED DESCRIPTION

For the purposes of promoting an understanding of the principles of the novel technology, reference will now be made to the embodiments illustrated in the drawings and specific language will be used to describe the same. It will nevertheless be understood that no limitation of the scope of the novel technology is thereby intended, such alterations and further modifications in the illustrated device, and such further applications of the principles of the novel technology as illustrated therein being contemplated as would normally occur to one skilled in the art to which the novel technology relates.

The present novel technology relates to a method of combination of organic and inorganic chemical systems in such a way as to eliminate the usual synthetic procedures requiring 1) temperature variations (both hot and cold), 2) the need for volatile solvents to effectuate dissolution of one or more phases to be blended, 3) vacuum or inert environment conditions to reduce oxygen or water vapor interaction, 4) templating molecules, 5) the usual overhead in terms of laboratory space, equipment, professional expertise in terms of synthesis. Additionally, the method may be easily scaled from the synthesis of gram amounts to the synthesis of tons, overcoming a production limitation that economically and operationally impedes the use of known functionalizing chemistries for large scale production of functionalized materials.

The present novel technology includes a method for producing a thermodynamically and kinetically stable material that slowly releases ions and moieties due to the complex chemistry created during the alloying process. The technique was developed to address a need for improved dental applications, and, accordingly, the following examples and embodiments tend to reflect chemistries having dental applications. However, the present novel method for producing functionalized chemistries is broadly applicable beyond the dental applications discussed herein.

Typically, the hybrid materials may coexist with fluoride and do not compromise fluoride bioavailability. The formation and/or retention of chemical structures facilitate and modulate interactions among the hybrid materials and other components when added to condensed phases. At the same time, the functionalized surface aids in promoting direct contact between a target material (such as a pellicle, enamel, intestinal walls or the like), and therefore allows for more efficient delivery of a desired active component.

The present novel technology may be used to generate functionalized hybrid materials on a nano-, meso-, and/or macroscale. The characteristics and properties of these materials typically include one or more of the following:
 the hybrid material improves remineralization efficacy by delivering small, surfactant-coated minerals to a substrate, such as dentition.
 the hybrid material is compatible with existing fluoride formulations so that increased benefit of bioavailable minerals, including calcium and fluoride, may be enjoyed.
 the synergistic effect of adding a functionalized nanomaterial to fluoride in a single treatment serves to improve oral health relative to existing treatments.

Mechanochemical Ball Milling

Mechanochemical (MC) ball milling not only reduces particle size but also impacts particles with sufficient force that such disparate materials as oxides, ceramics, organic powders and the like maybe chemically combined together to form new alloys or composites. This mechanochemical synthesis process occurs entirely in the solid state. This capability separates MC ball mills from traditional mills. This destructive process deforms components through powerful collisions between ball-particle, particle-wall, and particle-particle. These collisions are sufficiently energetic to give rise to the formation of significant grain boundaries at the nanoscale where components have fractured and fused. In order to generate the energy required for such concurrent fracturing and fusion, the vessel containing the balls and material is typically rotated at high speed opposite to the direction of rotation of the platform on which the vessel is placed (i.e., mimicking 'tilt-a-whirl' motions). More particularly, the vessel is rotated in a first direction about an axis of rotation not passing through the vessel (i.e., the axis of rotation of the platform) while simultaneously rotated or spun in a second direction (i.e., about a second axis of rotation that is nonparallel to the first axis of rotation and typically, though not necessarily, passes through the vessel) to impart sufficient kinetic energy to the admixture within the vessel to both break down the precursor component parts of the admixture and fuse them together to generate a new hybrid compound.

The resultant hybrid nanomaterials formed from these concurrent physical and chemical processes enable material synthesis to extend beyond both what is typical of usual wet laboratory synthetic procedures and of ball milling in a wet medium. For example, one such opportunity relates to the extraction of elements from fluorescent powder for energy conservation. Additionally, MC ball milling has been employed to improve nitrogen absorption characteristics of getter materials as well as to synthesize nanoscale graphite platelets as an alternative to carbon nanotubes.

Milling additives have been used in MC ball milling to improve properties of the milled material, but these additions have been primarily directed at expediting particle size reduction. The present novel technology uses MC ball milling for more than the simple reduction of the physical dimensions of the particles, but instead as a starting point for specific chemical modification to generate novel materials with improved properties and characteristics, such as when added to various formulations.

One benefit of using the present high-energy milling method as an environment for fostering solid-state nanoscale chemical reactions is that MC milling is readily scaleable to met industrial demands. Typically, one robust industry-scale planetary ball mill has a commercial capacity ranging between 100 and 900 liters, and MC milling technology is currently used in developing improved nanosized pigments for coatings, lotions, and paints.

The current novel technology introduces efficiencies of cost, time, and scale of producing functionalized hybrid moieties without the need for complex and sophisticated wet chemistries. The resulting scaleablity may then be realized for various applications, for example where localized, slow-releasing chemical, mineral or drug delivery is desired. Functionalizing systems to specifically adsorb to target areas offers alternatives for more effective therapeutic or chemical treatments.

The novel chemical synthesis method exploits the mechanochemical ball milling process to produce a relatively great amount of relatively inexpensive functionalized complexes. Typically, the functionalized complexes are blends of independent organic and inorganic reagents coupled together to yield a hybrid material with enhanced properties. A typical inorganic material includes a calcium phosphate mineral such as calcium phosphate tribasic, calcium phosphate dibasic, dicalcium phosphate, and the like. Alternatively, other inorganic materials may include sodium, magnesium, iron, silicon, aluminum, manganese, titanium and the like in various mineralogical forms (carbonates, nitrides and the like).

Typical organic materials include anionic surfactants (such as sodium lauryl sulfate, sodium lauryl ether sulfate, ammonium lauryl sulfate, N,N-Dimethyl-N-[3-(sulfoxy)propyl]-1-nonanaminium hydroxide inner salt, sodium dodecylbenzenesulfonate, poly(ethylene glycol) 4-nonylphenyl 3-sulfopropyl ether potassium salt, doctyl sulfosuccinate sodium salt, and the like), cationic surfactants (such as pyridinium chloride, hexadecyltrimethylammonium bromide, N,N-cimethyl-N-[3-(sulfoxy)propyl]-1-decanaminium hydroxide inner salt, and the like), neutral surfactants—polyethers or polyesters (such as polyethylene glycol, polypropylene glycol (PPG), poly(ethylene glycol)-block-poly(propylene glycol)-block-poly(ethylene glycol), poly(ethylene oxide)-block-polycaprolactone, polycaprolactone diol, polycaprolactone triol, and the like), carboxylic acids (such as fumaric acid, acrylic acid, malic acid, citric acid, maleic acid, stearic acid, and the like), polymethyl methacrylate, or the like. In other words, the organic materials may include those with properties akin to the anionic surfactants listed above (i.e., materials having anionic terminal groups (such as sulfates, sulfonates, or carboxylates), having cationic species ionically bound (such as sodium or potassium ions), having aliphatic chain lengths up to 12 carbon atoms or even more, and/or having the character of sodium lauryl sulfate in its structures (such as sodium laureth sulfate, which manifests n-number of ethoxy groups ($OCH_2CH_2)_n$)), having properties akin to the cationic surfactants listed above (i.e., having quaternary ammonium cation character manifested in a conjugated carbon ring, having anionic species ionically bound (such as chlorine and bromide ions), and/or having aliphatic chain lengths up to 17 carbon atoms or more), having properties akin to the polyether surfactants listed above (i.e., having no charges manifested in its structure (i.e. they are neutral), terminated with hydroxyl groups (i.e. OH), having ether monomer lengths from n=about 13 to n=about 150, and/or having the ether linkage (C—O—C)), having properties akin to the polyester surfactants listed above (i.e., having no charges manifested in its structure (i.e. they are neutral), having ester monomer lengths from n=about 10 to n=about 150, and/or having the non-ring ester linkage (O—$(CH_2)_5$—C=O)), organic acids, and the like. For example, hybrid polymer-calcium phosphate systems may be produced in various formulations for improving remineralization efficacy of a fluoride rinse or paste or reducing tooth sensitivity in a paste or varnish.

Hybrid Synthesis

The preparation of organic-inorganic materials via a mechanochemical process is described as follows. Depending upon the desired composition, the mixture may range from between about 0.5 and 99.5 weight percent inorganic precursor material, with the balance being organic precursor material. In this example, the inorganic starting material is tricalcium phosphate, while the organic starting material is polyethylene glycol; however, any convenient inorganic and organic precursors may be selected. Tricalcium phosphate (TCP, $Ca_3(PO_4)_2$) may be purchased from a chemical vendor directly or may be formed by adding equal masses of calcium carbonate ($CaCO_3$) and dibasic calcium phosphate ($CaHPO_4.2H_2O$) to a refractory crucible and heating the mixture in an oven at about 1050° C. for about 24 hours to produce a resultant flaky, stiff powder crystalline TCP. TCP plus polyethylene glycol (PEG) having any one of various molecular weights (such as 600, 1500, and 6000 Da) may be added to a stainless steel vessel containing a plurality of milling media balls, such as about twenty-five 10 millimeter diameter stainless steel balls. PEG is typically substituted for TCP between 0 and 20 weight percent (wt. %). Additionally, a small amount of organic solvent, such as pentane, may be added to not only swell the PEG to encourage more uniform blending, but also to help prevent powder from caking onto the balls and walls of the vessel. Once loaded with the chemical precursors and milling media, the vessel is typically locked onto the sun wheel of a planetary ball mill. The vessel is then rotated unidirectionally and opposite the rotational direction of the sun wheel at a sufficiently high speed for a duration of time sufficient to yield functionalized chemical moieties, such as, for example, at about 550 rpm or more for about two hours. At the end of the milling process the resulting powders are then filtered from the balls and stored, such as in plastic containers.

In laboratory testing, particle-size measurements of so-produced powders typically revealed particle size distributions between 100 and 1000 nm, depending on the powder formulation. Even smaller sizes along grain boundaries may exist due to extensive breakdown and recombination or 'welding' of the particulates during the MC milling process.

Also, the texture and appearance of the powders may vary considerably with the composition of the selected organic and inorganic precursors, the milling media composition, size and number, the milling energy, the milling time, and like factors. For instance, milling the TCP powder in the absence of PEG typically produces fine, hard particles, while milling in the presence of PEG, however, powders that vary from fluffy and soft to inflexible and coarse with increasing PEG molecular weight and content. These rudimentary powder observations suggest a composite-like material might have been formed, as neither the singular forms of TCP nor the PEG exhibit such characteristics.

Functionalized Calcium Phosphate Hybrid Materials

The integrity of the $P_2O_5$ network and calcium environments inherent to a calcium phosphate mineral can be modified with the addition of an organic additive (e.g., a polymer having varied molecular weight and chemical character, a surfactant such as SLS, and a carboxylic acid such as fumaric acid) and prepared under a variety of milling conditions. During the milling event, solid-state interactions between the calcium phosphate material and the organic component create functionalized calcium phosphate hybrid materials with widely varying chemical and physical properties depending on material components and milling conditions. Spectroscopic investigations show that the microstructure of the resultant hybrid material after a milling event is unique to the singular structures of both the calcium phosphate mineral as well as the organic component; additionally, the structures vary significantly from one hybrid to another depending on the additive and milling conditions. Also, the texture, solubility, and particle-size of the resultant functionalized calcium phosphate materials also vary considerably. One benefit of these structural modifications is the resulting compatibility of the functionalized calcium phosphate with bioavailable fluoride. Another benefit is that the functionalized calcium phosphate can enhance the action of fluoride when interfaced with a substrate, such as the enamel and dentin of the tooth. The impact of these structural modifications on the resultant functionalized composition's interaction with fluoride and the dentition (enamel, dentin) has been examined using FDA-based and scientifically-accepted dental testing models and methods, and is discussed below.

Functionalized Calcium Phosphate Stability with Fluoride

Example 1

Typically to be considered a candidate in improving the effectiveness of a fluoride-based formulation, it is generally required that any added materials to the formulation do not inhibit the bioavailability (typically greater than ±50% of the theoretical ppm level, more typically greater than ±10% of the theoretical ppm level) or action of fluoride. A pilot study assessing the compatibility potential of a TCP (tricalcium phosphate)-PEG (polyethylene glycol) nanocomplex material prepared according to the novel methodology herein when added to NaF(aq) over a period of 26 days did not reduce fluoride bioavailability greater than 10%, while a soluble form of calcium acting as a control reduced bioavailable fluoride nearly 60%. The TCP and PEG precursors were introduced into a MC mill and were milled with sufficient energies to break down the organic and inorganic precursors into organic and inorganic components and fuse or couple the components to form functionalized complexes or moieties. Other compatibility studies with different functionalized calcium phosphates (for example, $TCP_{98}SLS_2$, which is a construct of 98% TCP plus 2% sodium lauryl sulfate, SLS) in the presence of 500, 1100, and 5000 ppm fluoride (from NaF)

have shown less than 10% bioavailable fluoride reduction over an accelerated aging period (temperature set to 40° C.) of at least 30 days (which is the equivalent to approximately 6 months at 20° C.).

Enamel Remineralization Via a TCP-PEG Additive Validated in a pH Cycling Lesion Reversal Model The following study was circulated to assess enamel remineralization effiacy of the functionalized hybrid calcium phosphate system relative to an unfunctionalized calcium phosphate system. The difference between post and baseline Vickers microhardness indentations was used as the analytical method assessing remineralization.

Hybrid Preparation:

The nomenclature to describe the test groups (2 and 3) in the cycling study showing the remineralization potential of the polymer-calcium phosphate hybrid is described as follows. TCP is tricalcium phosphate and $TCP_xPEG_y$ represents an alloyed material comprised of 1500 Da PEG, where x represents the weight percent of TCP in the composite (i.e. 95%) and y represents the fraction of PEG (i.e. 5%).

The test materials (groups 2 and 3) were prepared using a solid-state mechanochemical milling procedure that pulverized 20 grams of thermally prepared TCP for 2 hours at 550 rpms, unidirectionally, using twenty-four 10 mm diameter stainless steel balls and 20 ml of pentane. After milling, the powder was extracted from the mill jar and placed in 120 ml plastic containers. Groups 2 and 3 had 0 and 5 wt. % of PEG added, respectively, to the TCP prior to the two hours of milling/alloying.

Enamel Specimen Preparation:

Enamel specimens (5 mm×5 mm) were removed from extracted bovine teeth and mounted in rods. The specimens were ground and polished to a high luster with Gamma Alumina using standard methods. Ten specimens per group were prepared for this study.

Initial Decalcification:

Artificial lesions were formed in bovine enamel specimens by a 96-hour immersion into 12.0 ml of a solution of 0.1 M lactic acid and 0.2% Carbopol C907 which has been 50% saturated with hydroxyapatite and adjusted to pH 5.0 at 37° C. The lesion surface hardness range was 20-50 and average lesion depth was approximately 70µ.

Test Group Formulations:

The mass of the treatment powders was 30 mg (for a weight fraction of 6% with respect to the 5 g of water). There were a total of 20 treatments per group. There were a total of 3 groups in this study and they are identified as follows:
Group 1: Water (negative control)
Group 2: TCP
Group 3: $TCP_{95}PEG_5$ Treatment Regimen:

The cyclic treatment regimen consisted of a 4.0 hour/day acid challenge in the lesion forming solution and four, one-minute dentifrice treatment periods. After the treatments, the specimens were rinsed with running distilled water and then placed back into the artificial saliva. The remaining time (~21 hours) the specimens were in an artificial saliva/remineralization system. The regimen was repeated for 5 days.

Remineralization Measurements:

Remineralization was determined by comparing the Vickers surface microhardness after treatment (post) to that before treatment (baseline).

Data Analysis:

The mean and SEM of each parameter for each group were calculated. The Student Q-test was used to assess the accuracy of the individual specimen measurements and ANOVA was used to verify significant differences among the groups (p<0.05). Multiple t-tests were performed to identify where the differences were. Group means and standard deviations were plotted to help illustrate significances.

Figure 1:
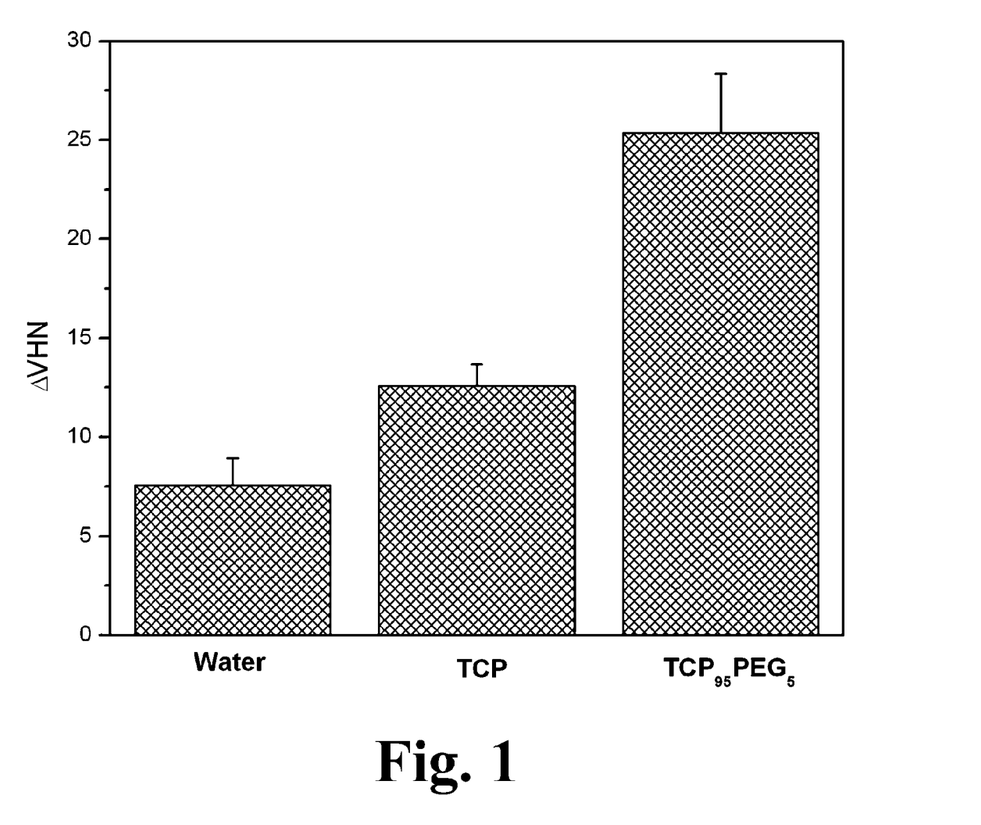
FIG. 1 is a graph showing the change in Vickers microhardness results from remin/demin cycling study including a negative control group (water) and positive control ACP and test group ACP95PEG15, comprised of 95 and 5 weight percent of TCP and 1500 Da PEG.

Results:

The results are charted below in FIG. 1, where the composition comprising 5 wt. % of 1500 Da PEG and 95 wt. % TCP is numerically and significantly different than both water (negative control) and unmodified TCP.

Conclusions:

The novel technology hybrid material prepared according to the novel methods disclosed herein may produce increased levels of remineralization relative to an unfunctionalized calcium phosphate when used in a standard pH cycling lesion reversal model.

Additives Comprised of Fumaric Acid and Tricalcium Phosphate and Validated in a Remineralization Model Example 2

Calcium phosphate additives were prepared by blending fumaric acid with tricalcium phosphate. The fumaric acid has a high melting point (~300 degrees Celsius) and manifests an unsaturated environment that can be activated to react with, for example, the tricalcium phosphate when subjected to high impact forces and energies inherent in the novel mechanochemical process discussed herein. The following data report the application findings when this high temperature, unsaturated organic molecule is blended forcibly with an inorganic salt (tricalcium phosphate) to yield a dental treatment complex and implemented into a tooth surface introduction medium, such as a fluoride-containing commercial varnish having 5% NaF.

Figure 2:
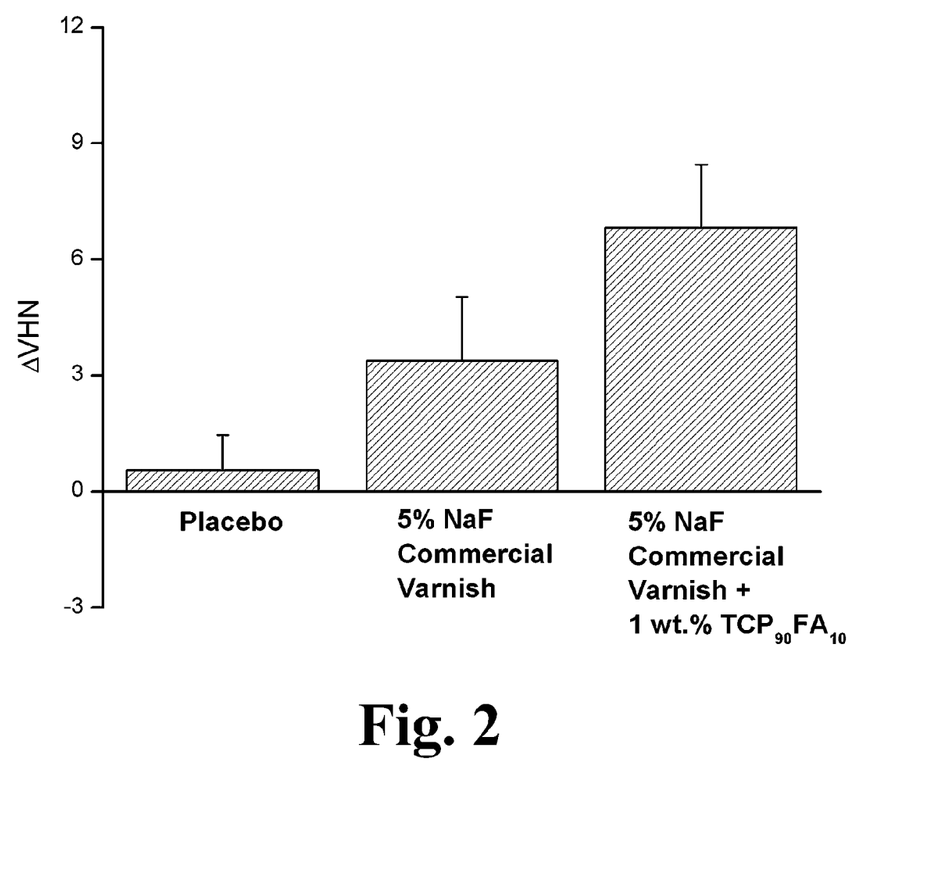
FIG. 2 is a graph showing the change in Vickers microhardness of human enamel after application of a 5% NaF commercially available varnish with and without the additive $TCP_{90}FA_{10}$, a construct of 90 wt. % TCP and 10 wt. % fumaric acid.

Ten enamel specimens were used in each group, with specimens initially demineralized for 18 hours at 37° C. in a carbopol-lactic acid demineralization solution (baseline microhardness values of enamel ranged between about 75 and about 115 Vickers Hardness Number, VHN). This challenge was performed to mimic softening of enamel due to early caries formation. Varnishes were left on enamel specimens for 24 hours and immersed in artificial saliva. After the 24-hour period the varnishes were removed and measured for Vickers surface microhardness (200 gf for 15 seconds). The change in VHN (i.e. post VHN−baseline VHN) are presented in FIG. 2. Statistical differences were found using Kruskal-Wallis One Way Analysis of Variance. The SNK method was used determine where the differences occurred (p<0.05). Only the 5% NaF Varnish+1 wt. % $TCP_{90}FA_{10}$ system was statistically different from the Placebo group; the other two groups were statistically equivalent (see FIG. 2).

Additives Comprised of Sodium Lauryl Sulfate, Cetylpyridinium Chloride, Polycaprolactone and Tricalcium Phosphate and Validated in a pH Cycling Lesion Reversal Remineralization Model Example 3

The use of prescription-based NaF toothpaste is suggested for certain population groups most at risk for developing caries. These pastes typically have 5000 ppm F and are used at least once daily as a replacement for the conventional 1100 ppm F paste in order to provide increased protection. To further increase protection, improved performance can be achieved with custom-made calcium phosphate additives that have been added to existing tooth care formulations, such as commercially available 5000 ppm F dentifrice formulations.

In one screening study, the extent of remineralization and fluoride uptake into white-spot enamel lesions when treated with modified tooth care formulations was investigated.

Experiment

The protocol for this screening study was performed as follows. Bovine enamel specimens were demineralized for 40 hours in a Carbopol-lactic acid 'white-spot' solution. White-spot lesions of approximately 70 microns were formed. The specimen microhardness ranged between 25 and 45 Vickers hardness numbers. Three enamel specimens were used for each of the treatment groups. The treatment groups consisted of a negative control (DI water), positive commercially available 5000 ppm F controls (product A and B), and experimental test groups comprised of commercially available product A combined with various additives. During treatment periods, artificial saliva was added to the test formulation in a 1:2 ratio (e.g. 5 g paste, 10 g artificial saliva).

The remineralization/demineralization pH cycling model used to evaluate the efficacy of the test groups is described as follows. Each 24-hour period consisted of four, two minute treatments from the groups described above, one, four-hour acid challenge emulating caries formation, and the remaining time the specimens were immersed in artificial saliva. The cycle was repeated for seven days, after which post microhardness and fluoride uptake measurements were performed on all enamel specimens.

Test Group Formulations:

There were a total of 6 groups in this study and they are identified as follows:

Group 1: Water (negative control)
Group 2: 5000 ppm F Commercial Product A
Group 3: 5000 ppm F Commercial Product B
Group 4: 5000 ppm F Product A+0.2% $TCP_{98}PCL_2$ [PCL=polycaprolactone]
Group 5: 5000 ppm F Product A+0.1% $TCP_{95}CPC_5$ [CPC=cetylpyridinium chloride]
Group 6: 5000 ppm F Product A+0.2% $TCP_{98}SLS_2$ [SLS=sodium lauryl sulfate]

Results

Figure 3:
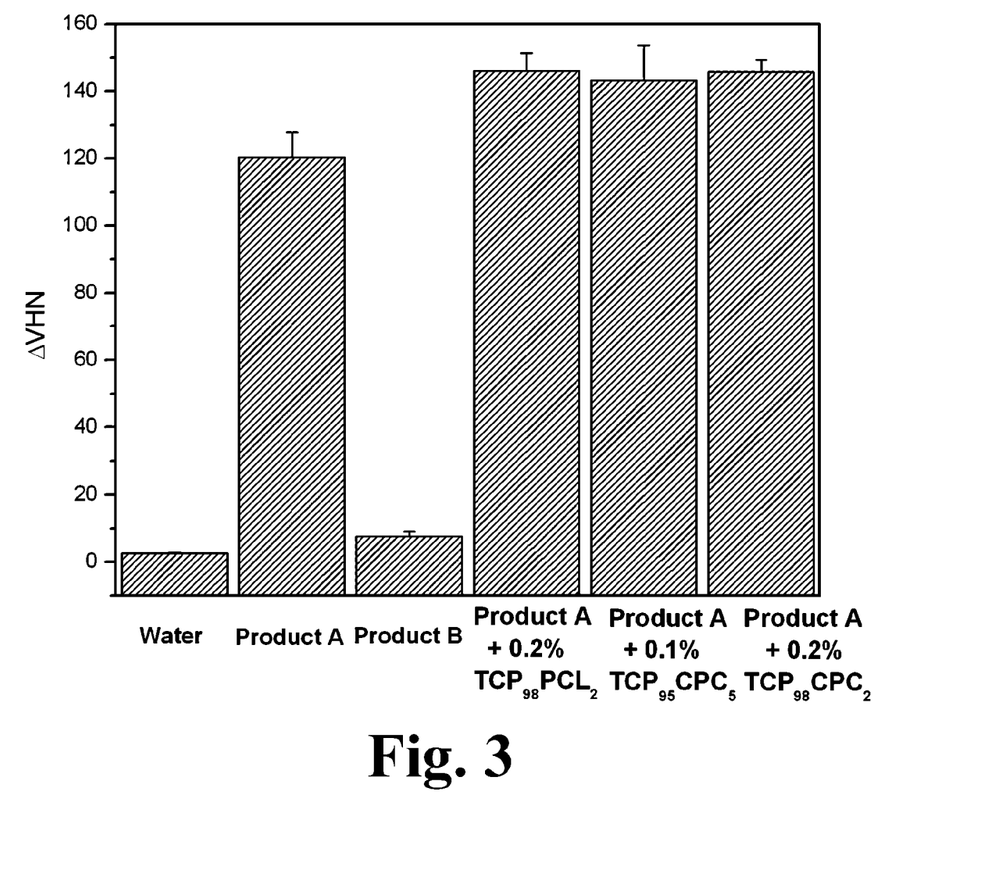
FIG. 3 is a graph showing the change in Vickers microhardness results after 7 days of a pH cycling lesion reversal dental model in experimental groups including commercially available 5000 ppm fluoride products A and B (positive controls) and Product A combined with different functionalized calcium phosphates: TCP98SLS2 [construct of 98% TCP plus 2% sodium lauryl sulfate, SLS], TCP98PCL2 [construct of 98% TCP plus 2% 2000 Da polycaprolactone, PCL], or TCP95CPC5 [construct of 95% TCP plus 5% cetylpyridinium chloride, CPC].

The extent of remineralization is the difference between post and baseline Vickers microhardness indentations of the enamel specimens and is reported as $\Delta VHN$. $\Delta VHN$ is plotted in FIG. 3 for the six groups listed above. Although only three specimens were used in each group in this pilot validation study, overall the relatively small standard errors suggest the microhardness range is acceptable for this study. The addition of functionalized calcium phosphate additives significantly improved the efficacy of the base 5000 ppm F Product A formulation by almost 30 VHN.

Figure 4:
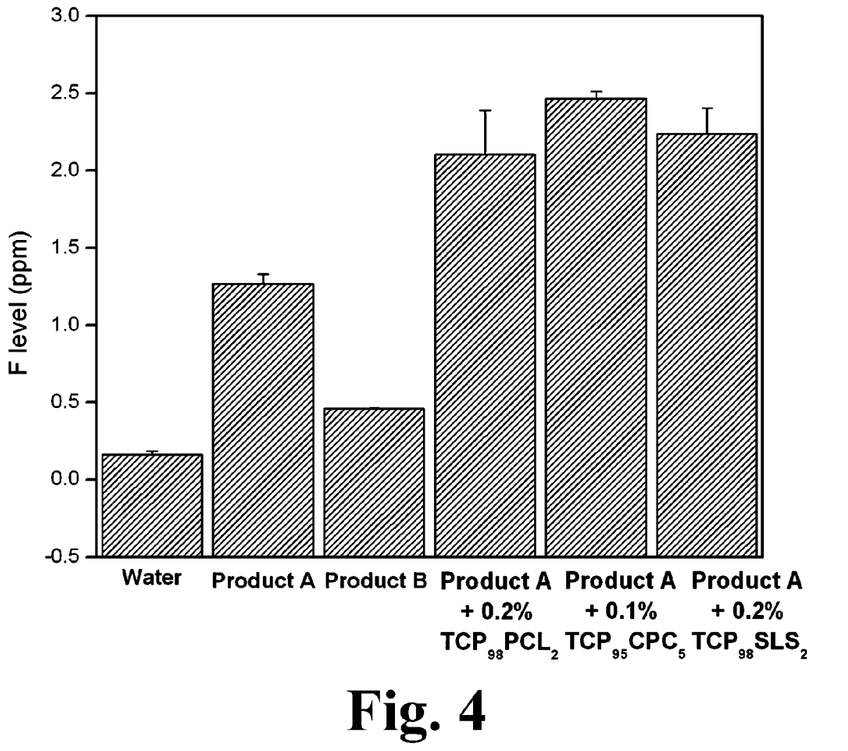
FIG. 4 is a graph showing enamel fluoride uptake results after 7 days of a pH cycling lesion reversal dental model in test groups including commercially available 5000 ppm fluoride products A and B, as well as Product A combined with different functionalized calcium phosphates: TCP98SLS2 [construct of 98% TCP plus 2% sodium lauryl sulfate, SLS], TCP98PCL2 [construct of 98% TCP plus 2% 2000 Da polycaprolactone, PCL], or TCP95CPC5 [construct of 95% TCP plus 5% cetylpyridinium chloride, CPC].

To further probe the remineralization efficacy, fluoride uptake measurements were made by drilling the enamel specimens, collecting the powder, and dissolving it in perchloric acid. The concentration of fluoride in the dissolved enamel was measured with a calibrated fluoride electrode and the results are presented in FIG. 4. These data show that the additives significantly increase fluoride incorporation into enamel almost twice as much as the base 5000 ppm F Product A formulation.

That fluoride-stable additives can improve fluoride uptake and remineralization and indicate that these agents function synergistically with the 5000 ppm F Product A formulation when examined in a seven day pH cycling model. The overall effect is a net remineralization of enamel. The additives do not appear to compromise and can improve the performance of Product A.

Performance in Occlusion of Dentin Tubules

Sound bovine dentin specimens 3 mm in diameter were extracted from teeth and mounted in rods. The specimens were ground and polished to a high luster with Gamma Alumina (0.050 microns) using standard methods.

The dentin specimens were initially demineralized for 10 minutes in dilute perchloric acid to dissolve calcium phosphate mineral within the tubes. After initial demineralization, baseline images were taken of each specimen using a reflective light microscope at 500× magnification. Ten specimens per group were prepared for each study. The groups were subjected to a 10-day pH cycling regimen consisting of two two-minute treatments and three three-minute acid challenge periods (COCA-COLA CLASSIC®, pH=2.65). (COCA-COLA CLASSIC is a Registered Trademark, Serial No. 74381727, of the COCA-COLA COMPANY, a Delaware Corporation, located at One Coca-Cola Plaza, Atlanta, Ga. 30313.) In between the treatments and acid challenges the specimens were immersed in artificial saliva. During the treatment period, the treatment pastes were diluted with DI water in a ratio of 1:3 (i.e. 5 ml of test solution: 15 ml DI water). The treatments consisted of: (a) a commercially available product for reducing dentinal hypersensitivity by occluding exposed dentinal tubules; (b) a similar product containing 1100 ppm fluoride to which 0.05% TCP98SLS had been added; (c) a similar product containing 5000 ppm fluoride; and (d) the latter product to which 0.1% TP98SLS2 had been added.

After the 10-day cycling period, specimens were examined optically. A second cycling study for five days was then employed to further improve mineral retention and/or formation in and on the dentin tubules. This study lacked acid challenges and instead consisted of three five-minute treatment periods.

After five days of cycling, images were taken again. The specimens were then subjected to one 30-minute treatment period (again a 1:3 dilution using DI water) and then immersed in artificial saliva and placed in an incubator at 37° C. for six days. During this time fresh artificial saliva was replaced daily. The specimens were then removed from the saliva after six days, lightly rinsed with DI water and dried in an oven at 37° C. for one hour. Optical images were then taken of the specimens.

The results of this study clearly indicated that the presence of the additives described in this invention enhanced the occlusion of the exposed dentinal tubules and therefore would be expected to decrease dentinal hypersensitivity more effectively than currently available products.

While the novel technology has been illustrated and described in detail in the foregoing examples, the same is to be considered as illustrative and not restrictive in character, it being understood that only the preferred embodiments have been shown and described and that all changes and modifications that come within the spirit of the novel technology are desired to be protected.

What is claimed is:

1. A solid-state method of producing functionalized compounds, comprising:
   placing a predetermined amount of crystalline tricalcium phosphate into a vessel rotatably connected to a turntable platform;
   placing a predetermined amount of an organic material into the vessel to define an admixture;
   placing milling media into the vessel;
   rotating the vessel in a first direction while turning the turntable platform in a second direction counter to the first direction;

milling the crystalline tricalcium phosphate and organic materials into smaller respective organic and crystalline tricalcium phosphate particles; and fusing portions of organic particles to crystalline phosphate particles to yield functionalized compounds;

wherein the particle size of a functionalized compound is at least 100 nanometers.

2. The method of claim 1, wherein the organic material is selected from the group consisting of anionic surfactants, cationic surfactants, neutral surfactants, carboxylic acids, polymers, copolymers, block copolymers, and combinations thereof.

3. The method of claim 1, wherein the vessel is operationally connected to a planetary ball mill; and wherein the vessel contains at least one grinding ball; wherein the vessel is rotated for a duration of at least 1 minute; and wherein the vessel includes a plurality of milling media; and wherein kinetic energy is imparted to the admixture by rotating the vessel in a first direction and simultaneously spinning the vessel in a second direction.

4. A solid state mechanochemical method for producing functionalized chemical compounds, comprising:

combining a first predetermined amount of crystalline tricalcium phosphate with a second predetermined amount of an organic material to yield an admixture;

placing the admixture in a reaction vessel;

imparting sufficient energy to the reaction vessel to at least partially convert at least some of the crystalline tricalcium phosphate and organic materials to respective intermediate crystalline tricalcium phosphate and intermediate organic particles of reduced size;

imparting sufficient kinetic energy to the respective crystalline tricalcium phosphate and organic intermediate particles to fuse at least some of the respective crystalline tricalcium phosphate and organic intermediate particles together to yield functionalized chemical compounds.

5. The method of claim 4 wherein the organic material is selected from the group consisting of neutral surfactants, carboxylic acids, negative surfactants, positive surfactants, and combinations thereof.

6. The method of claim 4 wherein the organic material is selected from the group consisting of fumaric acid, acrylic acid, malic acid, citric acid, maleic acid, stearic acid and combinations thereof.

7. A solid-state method of producing fluoridated functionalized compounds, comprising:

a) combining a first predetermined amount of crystalline tricalcium phosphate with a second predetermined amount of an organic material to define an admixture;

b) placing the admixture in a milling vessel operationally connected to a planetary mill;

c) introducing milling media into the milling vessel;

d) milling the admixture to impart sufficient kinetic energy to break down the organic material and crystalline tricalcium phosphate into substantially smaller intermediate particles;

e) milling the admixture with sufficient energy to fuse the intermediate particles together to yield functionalized molecules having both organic and crystalline tricalcium phosphate chemical characteristics f) combining the functionalized molecules having both organic and crystalline tricalcium phosphate characteristics with a fluoridated formulation to yield a fluoridated hybrid compound.

8. The method of claim 7 wherein the fluoridated hybrid compounds comprises between 0.5 and 99.5 weight percent of crystalline tricalcium phosphate and between 0.5 and 99.5 weight percent of an organic material.

9. The method of claim 7 wherein the organic material is a carboxylic acid and is selected from the group consisting of fumaric acid, acrylic acid, malic acid, citric acid, maleic acid, stearic acid and combinations thereof.

10. A solid-state method of producing functionalized compounds, comprising:

a) combining a predetermined amount of crystalline tricalcium phosphate with a predetermined amount of an organic material to yield an admixture;

b) placing the admixture in a milling vessel;

c) introducing milling media into the milling vessel;

d) milling the admixture to break down the organic and inorganic crystalline tricalcium phosphate materials into substantially smaller intermediate particles; and e) milling the admixture to fuse the intermediate particles together to yield functionalized compounds having both organic and inorganic crystalline chemical characteristics and a particle size of at least 100 nanometers.

11. The method of claim 10 and further comprising:

f) milling the functionalized compounds with a fluoridated formulation to yield a fluoridated hybrid compound.

12. The method of claim 10 wherein the functionalized compounds comprise between 0.5 and 99.5 weight percent of tricalcium phosphate and between 0.5 and 99.5 weight percent of an organic component.

13. The method of claim 10 wherein the organic material is selected from the group consisting of fumaric acid, acrylic acid, malic acid, citric acid, maleic acid, stearic acid and combinations thereof.

* * * * *